US00PP08074P

United States Patent [19]

Walters, deceased

[11] Patent Number: Plant 8,074

[45] Date of Patent: Dec. 22, 1992

[54] VARIETY OF GERANIUM NAMED DUCHESS

[75] Inventor: Ernest Walters, deceased, late of Hucknall, Great Britain, by Mary Bodill, administrator

[73] Assignee: Oglevee, Ltd., Connellsville, Pa.

[21] Appl. No.: 700,212

[22] Filed: May 13, 1991

[51] Int. Cl.[5] ..... A01H 5/00

[52] U.S. Cl. ..... Plt./87.12

[58] Field of Search ..... Plt./68, 87.12

*Primary Examiner*—Howard J. Locker

*Attorney, Agent, or Firm*—Webb, Burden, Ziesenheim & Webb

[57] ABSTRACT

The variety is characterized by its ability to root quickly and easily, as well as its prolific flowering. The abundance of florets are slow to shatter appearing as a deep pink and white flower atop a neat mound of medium green foliage which has a pleasant citrus fragrance.

1 Drawing Sheet

BACKGROUND OF THE INVENTION

The present invention comprises a new and distinct cultivar of *Pelargonium*×*domesticum* known by the varietal name Duchess (Oglevee No. 424; Walters No. 36W-O). The new variety was discovered in a selected breeding program by Mr. Ernest Walters in Hucknall, Nottingham, Great Britain. The new variety is a selection from the crossing of *P. crispum*×Prince William. The new variety was first asexually reproduced in the United States by cuttings at Oglevee, Ltd., Connellsville, Pa. in January of 1987. The new variety has been asexually reproduced by cuttings at Oglevee, Ltd. in Connellsville, Pa. over a several year period. It has also been trialed at Connellsville and has been found to retain its distinctive characteristics through successive propagations.

The cultivar when grown in a glass greenhouse in Connellsville, Pa. using natural light and 60° F. night and 68° F. day, has a response time of 14 weeks from a rooted cutting, not pinched, to flowering in a 6 inch pot. The response time was determined on plants grown in soilless media employing constant fertilizer 150–200 parts per million of nitrogen and potassium in full light. The rooted cuttings were potted on Nov. 1, 1989 and flowered on Feb. 15, 1990.

DESCRIPTION OF THE DRAWINGS

The accompanying photographic drawing illustrates the new cultivar, with the colors set forth therein being as nearly true as possible with color illustrations of this type.

DESCRIPTION OF THE NEW PLANT

The following detailed description sets forth the characteristics of the new cultivar. The data which defines these characteristics were collected by asexual reproductions carried out by Oglevee, Ltd. in Connellsville, Pa. The plant history was taken on fourteen week plants blossomed under natural light in a greenhouse and the color readings were taken indoors under 200–220 foot candles of florescent cool white light. Color references are primarily to the RHS Color Chart of The Royal Horticultural Society of London.

THE PLANT

Classification:

*Botanical.*—*Pelargonium*×*domesticum.*

*Commercial.*—*Regal geranium.*

Form: Upright, mount shaped habit.

*Height.*—28 cm from media surface.

*Growth.*—Strong, wiry but controlled growth.

Strength: Quick rooting, prolific flowering; artificial support not needed.

Foliage: Stalked leaf attachment.

Leaves:

*Size.*—7.5 cm–10.5 cm.

*Shape.*—Depressed ovate. Base: Truncate.

*Margin.*—Serrately lobed.

*Texture.*—Leathery; faintly pubescent; slightly reflective.

*Color.*—Top: Yellow/Green Group 144A. Bottom: Yellow/Green Group 146C.

*Ribs and veins.*—Palmate Venation. Color: Yellow/Green Group 147C.

Petioles: Length: 4.0 cm to 7.5 cm.

Stem:

*Color.*—Yellow/Green Group 146D.

*Internodes.*—1.0 to 1.5 cm between nodes.

THE BUD

Shape: Elliptical.

Size: 1.5 cm to 2.0 cm in length; bud just beginning to show color.

INFLORESCENCE

Blooming habit: Many small florets opening slowly to eventually form a full long-lasting flowerhead.

Size: 8.5 to 9.0 cm across.

Borne: Umbel; 3.0 cm to 4.0 cm above foliage; florets on pedicel, pedicel on peduncle.

Florets:

*Form.*—Cupped.

*Color.*—Top: Outside margin Red/Purple Group 73D to white. Center: blotch Red/Purpose Group 61B. Bottom: White margin with Red/-Purple Group 60C blotch.

*Petals.*—5 in number; single, not united; margin entire.

*Size.*—3.5 cm to 4.0 cm across when fully open.

*Texture and appearance.*—Smooth; appearance from a distance is a deep pink and white flower atop a neat mount of medium green foliage.

Petaloids:

*Quantity.*—None.

Pedicel:

*Length.*—1.5 cm to 2.0 cm.

*Color.*—Yellow/Green Group 146C.

Peduncle: Arises from node opposite leaf petiole.

*Color.*—Yellow/Green Group 146C.

*Length.*—3.5 cm to 4.0 cm.

Disease resistance: Not known.

Lasting quality: Very slow to shatter, continuous blooming.

REPRODUCTIVE ORGANS

Stamens:

*Anthers.*—2.0 mm to 3.0 mm in length.

*Filaments.*—White at base to pale pink at other end; flat, varying lengths 0.6 mm to 1.6 mm.

*Pollen.*—Golden Brown/Greyed Orange Group 171B.

Pistils:

*Number.*—1.

*Length.*—1.5 cm.

*Stigma.*—5 to 6 parted, red/purple in color.

*Style.*—1.0 to 1.2 cm in length, red/purple in color.

Ovaries: Pale green; superior; very pubescent; 5.0 mm to 6.0 mm in length; 2.0 mm to 3.0 mm across.

Fruit: None observed.

GENERAL CHARACTERISTICS

This new variety of *Pelargonium*×*domesticum* improves many qualities of the known Regal geraniums. It roots with more ease and quickness. It branches eagerly which increases cutting production. It flowers over a longer period of time with an abundance of dainty florets and shatters less quickly. The foliage is that of a neat uniform mound shape and has a pleasant citrus fragrance.

I claim:

1. A new and distinct variety of geranium plant, substantially as shown and described.

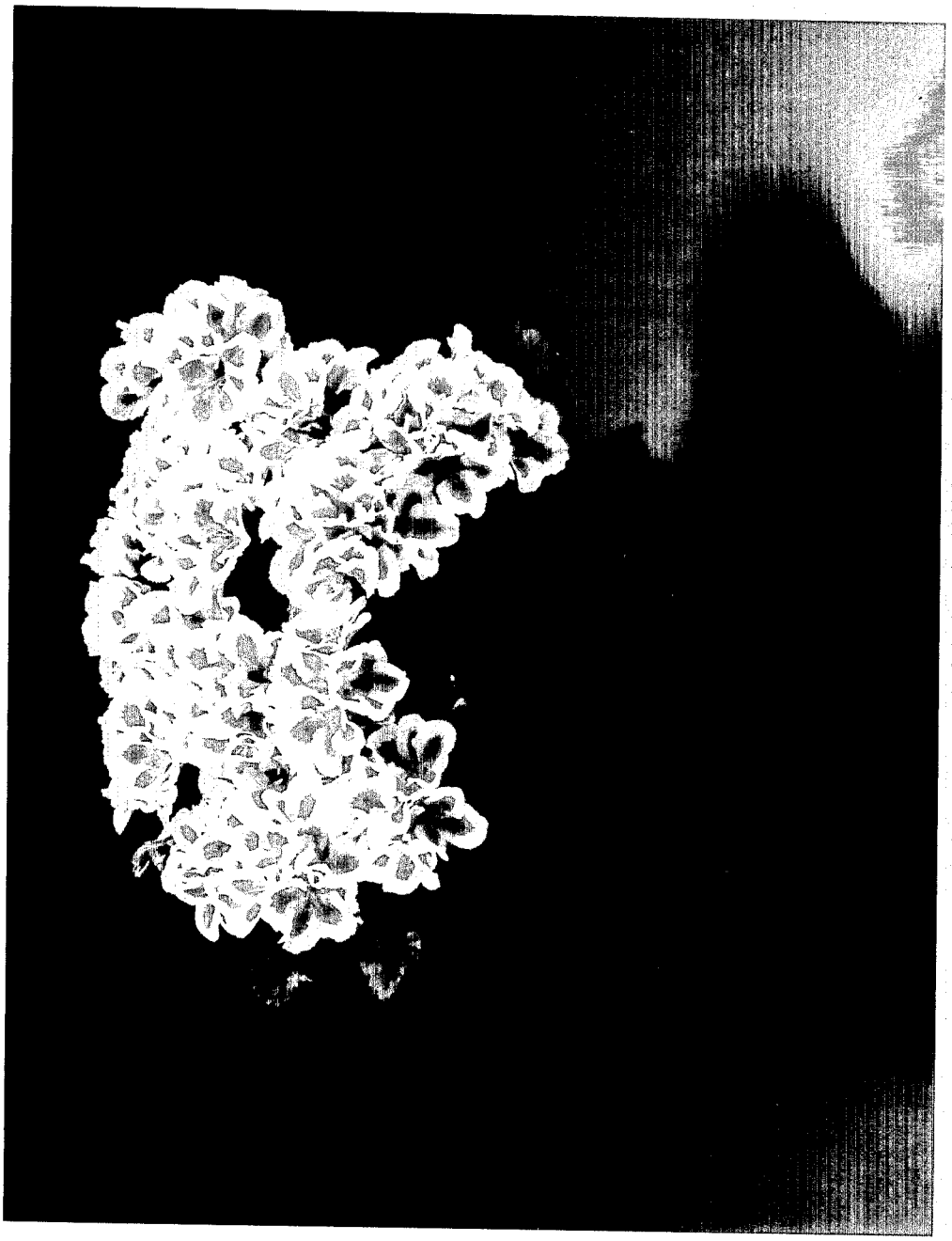

* * * * *